United States Patent [19]
Müller-Gliemann et al.

[11] Patent Number: 5,935,983
[45] Date of Patent: *Aug. 10, 1999

[54] USE OF PHENYLCYCLOHEXYLCARBOXAMIDES

[75] Inventors: Matthias Müller-Gliemann, Solingen; Ulrich Müller, Wuppertal, both of Germany; Martin Beuck, Milford, Conn.; Siegfried Zaiss, Wuppertal, Germany; Christoph Gerdes, Leverkusen, Germany; Anke Domdey-Bette, Hückeswagen, Germany; Rudi Grützmann, Solingen, Germany; Stefan Lohmer, Milan, Italy; Stefan Wohlfeil, Hilden; Özkan Yalkinoglu, Wuppertal, both of Germany; James Elting, Madison, Conn.; Dirk Denzer, Wuppertal, Germany

[73] Assignee: Bayer Aktiengesellschaft, Leverkusen, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 08/960,075

[22] Filed: Oct. 24, 1997

Related U.S. Application Data

[63] Continuation of application No. 08/588,477, Jan. 18, 1996, abandoned.

[30] Foreign Application Priority Data

Feb. 1, 1995 [DE] Germany .......................... 195 03 160

[51] Int. Cl.$^6$ ...................... A61K 31/415; C07D 235/18; C07D 235/08
[52] U.S. Cl. .......................... 514/397; 548/309.7
[58] Field of Search .......................... 514/397; 548/309.7

[56] References Cited

U.S. PATENT DOCUMENTS 5,395,840  3/1995  Müller et al. .

FOREIGN PATENT DOCUMENTS

| 42 26 109 | 2/1994 | Germany . |
| 44 01 893 | 7/1995 | Germany . |
| 9418968 | 2/1994 | WIPO . |

OTHER PUBLICATIONS

R. Ross, The Journal of Cell Biology, vol. 50, pp. 172–186, (1971).

*Primary Examiner*—Patricia L. Morris
*Attorney, Agent, or Firm*—Sprung Kramer Schaefer & Briscoe

[57] ABSTRACT

The phenylcyclohexylcarboxamides, some of which are known, are suitable as active compounds in medicaments, in particular in medicaments for the treatment of restenosis.

9 Claims, No Drawings

USE OF PHENYLCYCLOHEXYLCARBOXAMIDES

This application is a continuation of application Ser. No. 08/588,477, filed Jan. 18, 1996, now abandoned.

The invention relates to the new use of phenylcyclohexylcarboxamides, to new substances and to processes for their preparation, in particular as medicaments for the treatment of restenosis.

It has been found that phenylcyclohexylcarboxamides of the general formula (I)

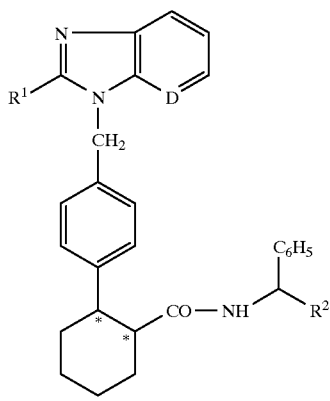

(I)

in which

D represents the —CH group or a nitrogen atom, $R^1$ represents phenyl, cycloalkyl having 3 to 6 carbon atoms or straight-chain or branched alkyl having up to 5 carbon atoms, $R^2$ represents straight-chain or branched alkoxycarbonyl having up to 5 carbon atoms, or a radical of the formula —CO—NH$_2$ or —CH$_2$—OH, and their salts, surprisingly cause a severe inhibition of the proliferation of smooth muscle cells and are thus suitable for use in the control of restenosis.

The phenylcyclohexylcarboxamides can also be present according to the invention in the form of their salts. In general, salts with organic or inorganic bases or acids may be mentioned here.

In the context of the present invention, physiologically acceptable salts are preferred. Physiologically acceptable salts of the compounds according to the invention can be salts of the substances according to the invention with mineral acids, carboxylic acids or sulphonic acids. Particularly preferred salts are, for example, those with hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, propionic acid, lactic acid, tartaric acid, citric acid, fumaric acid, maleic acid or benzoic acid.

Physiologically acceptable salts can also be metal or ammonium salts of the compounds according to the invention which have a free carboxyl group. Particularly preferred salts are, for example, sodium, potassium, magnesium or calcium salts, and also ammonium salts which are derived from ammonia, or organic amines, such as, for example, ethylamine, di- or triethylamine, di- or triethanolamine, dicyclohexylamine, dimethylaminoethanol, arginine, lysine, ethylenediamine or 2-phenylethylamine.

The compounds can be used according to the invention in stereoisomeric forms which either behave as image and mirror image (enantiomers), or which do not behave as image and mirror image (diastereomers). The invention relates both to the enantiomers or diastereomers and their respective mixtures. Just like the diastereomers, the racemic forms can be separated into the stereoisomerically uniform constituents in a known manner.

The use is preferred of compounds of the general formula (I), in which

D represents the —CH group or a nitrogen atom, $R^1$ represents phenyl, cyclopropyl, cyclopentyl, cyclohexyl or straight-chain or branched alkyl having up to 4 carbon atoms, $R^2$ represents straight-chain or branched alkoxycarbonyl having up to 4 carbon atoms, or a radical of the formula —CO—NH$_2$ or —CH$_2$—OH, and their salts, in the control of restenosis.

The use is particularly preferred of compounds of the general formula (I), in which D represents the —CH group or a nitrogen atom, $R^1$ represents phenyl, cyclopropyl, ethyl or iso-propyl, $R^2$ represents straight-chain or branched alkoxycarbonyl having up to 4 carbon atoms, or a radical of the formula —CO—NH$_2$ or —CH$_2$—OH, and their salts, in the control of restenosis.

The invention additionally relates to new compounds of the general formula (I) having the substituent meanings indicated in the following table:

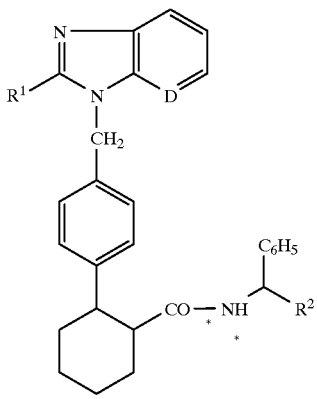

(I)

| $R^1$ | D | $R^2$ | Isomer |
|---|---|---|---|
| cyclopropyl | CH | —CH$_2$—OH | dia A, S |
| cyclopropyl | CH | —CH$_2$—OH | dia B, S |
| —CH(CH$_3$)$_2$ | N | —CH$_2$—OH | dia A, S |
| —CH(CH$_3$)$_2$ | N | —CH$_2$—OH | dia B, S |
| —CH(CH$_3$)$_2$ | CH | —CH$_2$—OH | dia A, S |
| —CH(CH$_3$)$_2$ | CH | —CH$_2$—OH | dia B, S |
| —C$_2$H$_5$ | N | —CH$_2$—OH | dia A, S |

3
-continued (I)

| R¹ | D | R² | Isomer |
|---|---|---|---|
| —C₂H₅ | N | —CH₂—OH | dia B, S |
| —C₂H₅ | CH | —CH₂—OH | dia A, S |
| —C₂H₅ | CH | —CH₂—OH | dia B, S |
| —C₆H₅ | CH | —CH₂—OH | dia A, S |
| —C₆H₅ | CH | —CH₂—OH | dia B, S |
| —CH(CH₃)₂ | CH | —CO₂CH₃ | dia |
| —CH(CH₃)₂ | CH | —CO—NH₂ | dia A |
| —CH(CH₃)₂ | CH | —CO—NH₂ | dia B |
| cyclopropyl | CH | —CO—NH₂ | dia |
| cyclopropyl | CH | —CO—NH₂ | dia B |
| —CH(CH₃)₂ | N | —CO—NH₂ | dia A |
| —CH(CH₃)₂ | N | —CO—NH₂ | dia B |
| —C₂H₅ | N | —CO—NH₂ | dia |
| —C₂H₅ | CH | —CO—NH₂ | dia A |
| —C₂H₅ | CH | —CO—NH₂ | dia B |
| —C₆H₅ | CH | —CO—NH₂ | dia |

The compounds of the general formula (I) are prepared by hydrolysing compounds of the general formula (II)

(II)

in which
R¹ and D have the meaning indicated, and
R³ represents straight-chain or branched $C_1$–$C_4$-alkoxy,
and reacting the acids, if appropriate with prior activation, in inert solvents, if appropriate in the presence of a base and/or of a dehydrating agent, with phenylglycine derivatives of the general formula (III)

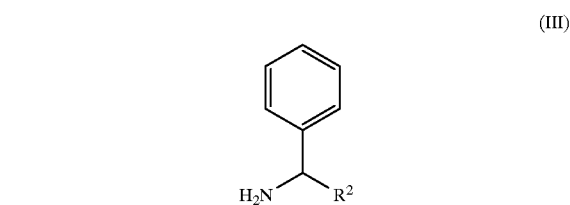

(III)

in which
R² has the meaning indicated, and if R²/R²'=—CO—NH₂, if appropriate, starting from the corresponding esters, carrying out a reaction with ammonia in alcohols.

The process according to the invention can be illustrated by way of example by the following reaction scheme:

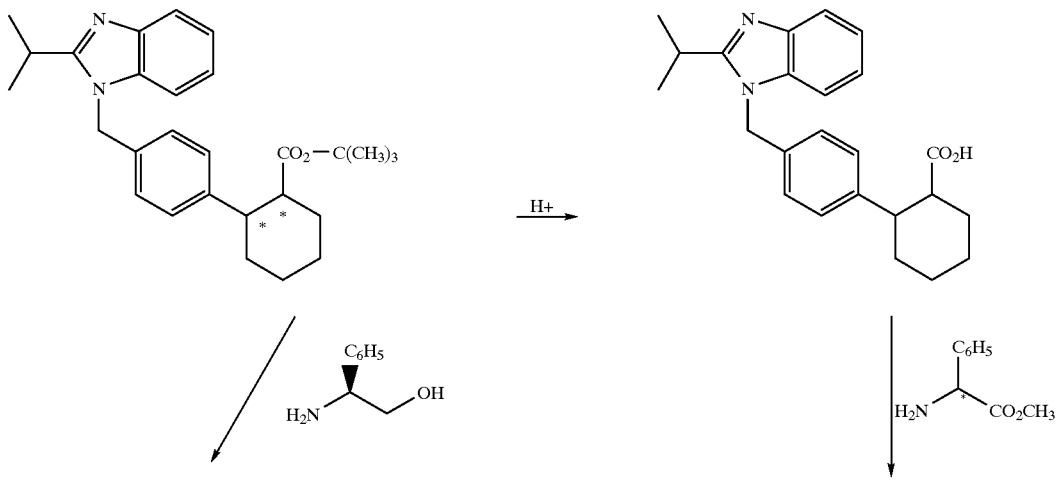

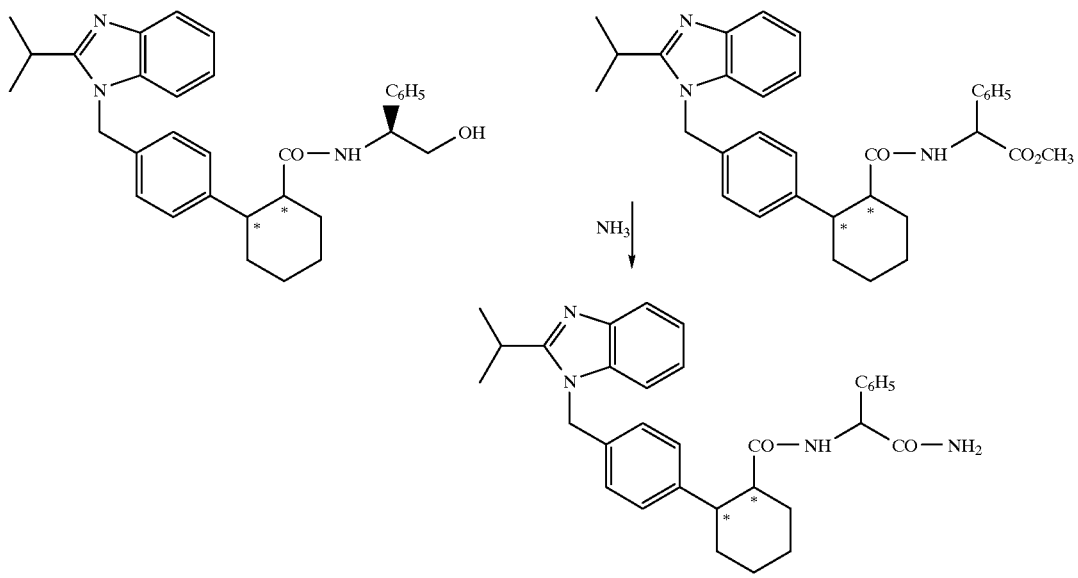

-continued

Suitable solvents for the process are customary organic solvents which do not change under the reaction conditions. These preferably include ethers such as diethyl ether, dioxane, tetrahydrofuran, glycol dimethyl ether, or hydrocarbons such as benzene, toluene, xylene, hexane, cyclohexane or petroleum fractions, or halogenohydrocarbons, such as dichloromethane, trichloromethane, tetrachloromethane, dichloroethylene, trichloroethylene or chlorobenzene, or ethyl acetate, triethylamine, pyridine, dimethyl sulphoxide, dimethylformamide, hexamethylphosphoramide, acetonitrile, acetone or nitromethane. It is also possible to use mixtures of the solvents mentioned. Dichloromethane and tetrahydrofuran are preferred.

Bases employed for the process according to the invention can in general be inorganic or organic bases. These preferably include alkali metal hydroxides such as, for example, sodium hydroxide or potassium hydroxide, alkaline earth metal hydroxides such as, for example, barium hydroxide, alkali metal carbonates, such as sodium carbonate, potassium carbonate or caesium carbonate, alkaline earth metal carbonates such as calcium carbonate, or alkali metal or alkaline earth metal alkoxides such as sodium or potassium methoxide, sodium or potassium ethoxide or potassium tert-butoxide, or organic amines (trialkyl($C_1$–$C_6$)amines) such as triethylamine, or heterocycles such as 1,4-diazabicyclo[2.2.2]octane (DABCO), 1,8-diazabicyclo[5.4.0]undec-7-ene (DBU), pyridine, diaminopyridine, methylpiperidine or morpholine. It is also possible as bases to employ alkali metals such as sodium or their hydrides such as sodium hydride. Preferred bases are sodium hydride, potassium carbonate, triethylamine, pyridine and potassium tert-butoxide.

In general, the base is employed in an amount from 0.05 mol to 10 mol, preferably from 1 mol to 2 mol relative to 1 mol of the compound of the formula (III).

The process according to the invention is in general carried out in a temperature range from −50° C. to +100° C., preferably from −30° C. to +60° C.

The process according to the invention is in general carried out at normal pressure. However, it is also possible to carry out the process at elevated pressure or at reduced pressure (e.g. in a range from 0.5 to 5 bar).

The amidation can optionally proceed via the activated stage of the acid halides or mixed anhydrides, which can be prepared from the corresponding acids by reaction with thionyl chloride, phosphorus trichloride, phosphorus pentachloride, phosphorus tribromide or oxalyl chloride or methanesulphonyl chloride.

Suitable bases for this in addition to the abovementioned bases are preferably triethylamine and/or dimethylaminopyridine, DBU or DABCO.

The base is employed in an amount from 0.5 mol to 10 mol, preferably from 1 mol to 5 mol, relative to 1 mol of the compounds of the general formula (III).

The acid-binding agents employed for the amidation can be alkali metal or alkaline earth metal carbonates such as sodium carbonate, potassium carbonate, alkali metal or alkaline earth metal hydroxides such as, for example, sodium or potassium hydroxide, or organic bases such as pyridine, triethylamine, N-methylpiperidine, or bicyclic amidines such as 1,5-diazabicyclo[4.3.0]non-5-ene (DBN) or 1,5-diazabicyclo[5.4.0]undec-7-ene (DBU). Triethylamine is preferred.

Suitable dehydrating reagents are carbodiimides such as, for example, diisopropylcarbodiimide, dicyclohexylcarbodiimide or N-(3-dimethylaminopropyl)-N'-ethylcarbodiimide hydrochloride, or carbonyl compounds such as carbonyldiimidazole or 1,2-oxazolium compounds such as 2-ethyl-5-phenyl-1,2-oxazolium-3-sulphonate or propanephosphonic anhydride or isobutyl chloroformate or benzotriazolyloxy-tris-(dimethylamino)phosphonium hexafluorophosphate or diphenyl phosphoramidate or methanesulphonyl chloride, if appropriate in the presence of bases such as triethylamine or N-ethylmorpholine or N-methylpiperidine or dicyclohexylcarbodiimide and N-hydroxysuccinimide.

The acid-binding agents and dehydrating reagents are in general employed in an amount from 0.5 to 3 mol, preferably from 1 to 1.5 mol, relative to 1 mol of the corresponding carboxylic acids.

The conversion to the corresponding phenylglycinamidoamides ($R^2/R^{2'}$=—$CONH_2$ is carried out using alcoholic ammonia, preferably ammonia-saturated alcohols, such as, for example, methanol or ethanol, preferably methanol, at room temperature.

The compounds of the general formula (III) are known or can be prepared by customary methods.

The compounds of the general formula (II) are new or can be prepared by reaction of compounds of the formula (IV)

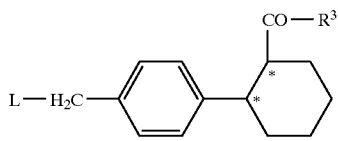

(IV)

in which

L represents a typical leaving group such as, for example, chlorine, bromine, iodine, tosylate or mesylate, preferably bromine, and $R^3$ has the meaning indicated above, with compounds of the general formula (V)

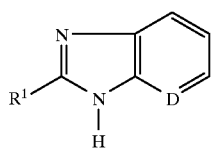

(V)

in which $R^1$ and D have the meanings indicated, in the solvents indicated above, if appropriate in the presence of the abovementioned bases.

The compounds of the general formula (I) surprisingly show an unforeseeable, useful spectrum of pharmacological action.

They inhibit the proliferation of smooth muscle cells and can therefore be employed for the treatment of restenosis.

The new substances can moreover be employed for the treatment of arteriosclerosis.

Investigation of the inhibition of the proliferation of smooth muscle cells by the compounds according to the invention To determine the antiproliferative action of the compounds, smooth muscle cells are used which are obtained from the aortas of pigs by the media explant technique [R. Ross, J. Cell. Biol. 50, 172, 1971]. The cells are inoculated into suitable culture dishes, as a rule 96-hole plates, and cultured at 37° C. in 5% $CO_2$ for 2–3 days in medium 199 containing 7.5% FCS and 7.5% NCS, 2 mM L-glutamine and 15 mM HEPES, pH 7.4. The cells are then synchronized by serum withdrawal for 2–3 days and then stimulated to growth using serum or other factors. Test compounds are added simultaneously. After 16–20 hours, $^3$H-thymidine is added and after a further 4 hours the incorporation of this substance into the TCA-precipitable DNA of the cells is determined. To determine the $IC_{50}$ values, the active compound concentration is calculated which, on sequential dilution of the active compound, causes half-maximal inhibition of the thymidine incorporation produced by 10% FCS.

TABLE A

| Example No. | $IC_{50}$ (nM) |
|---|---|
| 16 | 0.28 |
| 19 | 0.01 |

Investigations of the inhibition of c-fos gene expression of smooth muscle cells by the compounds according to the invention The antiproliferative action of the compounds was investigated with respect to the serum- and growth factor-mediated signal transduction and induction of c-fos gene expression in smooth muscle cell reporter lines. The reporter used in this connection is luciferase, whose expression is controlled by means of the human c-fos promoter. The c-fos promoter/luciferase construct is stably integrated into the chromosomal DNA of the rat smooth muscle cell line A 10 (ATCC CRL 1476). The reporter cells are inoculated into 96-hole plates and cultured at 37° C. in 5% $CO_2$ for 1–2 days in serum-containing medium (D-MEM containing 10% FCS, 2 mM L-glutamine and 15 mM HEPES, pH 7.4). To suppress the c-fos promoter activity to basal values, the cells are arrested by serum withdrawal for 24 hours. Test compounds are then added, and the cells are stimulated with FCS or growth factors to induce luciferase activity. After this treatment period (4 hours) the cells are lysed and their extracts are employed for the luciferase determination. The $IC_{50}$ values are calculated from the active compound concentration which, on sequential dilution of the active compound, causes the half-maximal inhibition of the luciferase activity produced by the particular stimulus.

In vivo investigations of the inhibition of vascular smooth muscle cell proliferation in the air-perfused rat carotid model The in vivo investigations of the inhibition of vascular smooth muscle cell proliferation in the air-perfused rat carotid model were carried out by the slightly modified method of Fishman et al. (Lab. Invest. 32, 339–351, 1975); the operation on the animals was carried out under Nembutal® anaesthesia. The right common carotid artery is exposed and clamped off using two vascular clamps at a caudal to cranial distance of about 1.5 cm. A cannula is inserted at the cranial end of this vascular segment and the caudal end is perforated by pricking with a needle. After rinsing with physiological saline solution, a stream of air (25 ml/min for 4 min) is perfused through the segment. The clamps are then removed, the bleeding is stopped with slight pressure and the operation field is closed with wound clamps. The animals are sacrificed eight days after the operation, and the previously air-perfused and, as a control, the corresponding contralateral carotid segments are removed.

The administration of the test substances (p.o, i.v., i.p., s.c.) was begun two days before the operation, and the treatment was then carried out over the entire experimental period (duration of treatment in total: 10 days).

The determination of the air-induced smooth muscle cell proliferation was carried out by means of the DNA content of the carotid segments according to Helms et al. (DNA 43, 39–49, 1985). To do this, the pieces of vessel are digested enzymatically using proteinase K, and the DNA is isolated and determined fluorometrically using bisbenzimide (DNA from herring sperm as standard). The DNA content of the vessels is finally indicated in µg of DNA per mm of carotid.

To determine the antiproliferative action of the compounds according to the invention, a balloon catheter is inserted into the carotid artery in rats and inflated, and the inside of the blood vessel is injured by moving the catheter [Clowes A. W., et al., Lab. Invest. Vol. 49, No. 3, p. 327, 1983]. This injury causes a neointimal smooth muscle proliferation, which produces stenoses. The extent of the vessel constriction in the animals is determined after about 2 weeks by histological working up of the blood vessels by measuring the surface area of the proliferation tissue on vessel cross-sections.

The new active compounds can be converted in a known manner into the customary formulations, such as tablets, coated tablets, pills, granules, aerosols, syrups, emulsions, suspensions and solutions, using inert, non-toxic, pharmaceutically suitable excipients or solvents. In this context, the therapeutically active compound should in each case be present in a concentration of about 0.5 to 90% by weight of the total mixture, i.e. in amounts which are sufficient in order to achieve the dosage range indicated.

The formulations are prepared, for example, by extending the active compounds with solvents and/or excipients, if appropriate using emulsifiers and/or dispersants, it optionally being possible, e.g. if water is used as a diluent, to use organic solvents as auxiliary solvents.

Administration is carried out in a customary manner, preferably orally or parenterally, in particular perlingually or intravenously.

In the case of parenteral administration, solutions of the active compound can be employed using suitable liquid excipient materials.

In general, it has proven advantageous in the case of intravenous administration to administer amounts of about 0.001 to 20 mg/kg, preferably about 0.01 to 5 mg/kg, of body weight to achieve effective results, and in the case of oral administration the dose is about 0.01 to 50 mg/kg, preferably 1 to 10 mg/kg, of body weight.

In spite of this, it may optionally be necessary to depart from the amounts mentioned, namely depending on the body weight and the type of administration route, on individual behaviour towards the medicament, the manner of its formulation and the time or interval at which administration takes place. Thus, in some cases it may be adequate to manage with less than the abovementioned minimum amount, while in other cases the upper limit mentioned must be exceeded. In the case of the administration of larger amounts, it may be advisable to divide these into several individual doses over the course of the day.

Solvents

A=dichloromethane: methanol: acetic acid 9:1:0.1
B=dichloromethane: methanol: ammonia 9:1:0.1
C=dichloromethane: methanol 95:5

Starting Compounds

EXAMPLE I

2-Isopropyl-benzimidazole

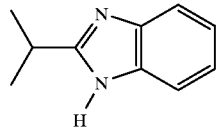

6.54 g (60 mmol) of 2,3-diaminopyridine, 5.6 g (60 mmol) of isobutyric acid and 45 ml of polyphosphoric acid are combined and heated at 130° C. for 6½ h. After 6.5 h, the mixture is added to 0.4 l of ice water, brought to pH 7 using solid NaOH, $Na_2CO_3$ is added until the evolution of gas is complete and the mixture is extracted three times with ethyl acetate. The combined organic phases are dried over $Na_2SO_4$ and concentrated.
Yield:
8.45 g (87% of theory)
$R_f$=0.36 ($CH_2Cl_2$/MeOH=9:1)

EXAMPLE II tert-Butyl trans-2-[4-(2-isopropylbenzimidazolyl-1H-methyl)phenyl]-cyclohexane-1-carboxylate

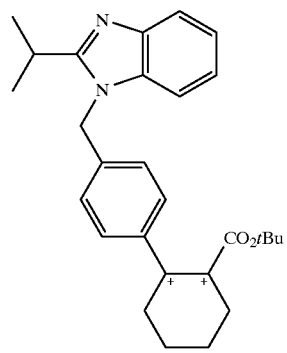

0.75 g of NaH (25 mmol, 80% strength) is suspended in 50 ml of DMF, cooled to −10° C. and treated dropwise at a maximum of 0° C. with a solution of 4.03 g (25 mmol) of 2-isopropylbenzimidazole in 60 ml of DMF. After stirring for 15 min, a solution of tert-butyl trans-2-(p-bromomethylphenyl)-cyclohexane-1-carboxylate in 110 ml of DMF is added at a maximum of 0° C. After stirring at RT for 2.5 h, the mixture is treated with 25 ml of 1 N HOAc and concentrated. The residue is partitioned in ether/water, the aqueous phase is extracted a further two times, the combined organic phase is dried over $Na_2SO_4$ and concentrated, and the product is purified on silica gel 60 (PE/EA=3:7).
Yield:
2.91 g (28% of theory)
$R_f$=0.73 ($CH_2Cl_2$/MeOH=9:1)

EXAMPLE III trans-2-[4-(2-Isopropylbenzimidazolyl-1H-methyl)-phenyl]-cyclohexanecarboxylic acid

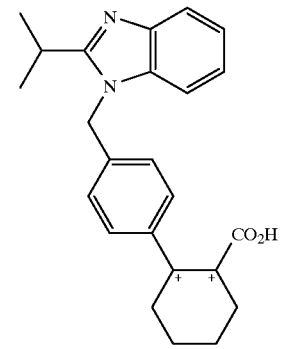

2.91 g (6.7 mmol) of the compound from Example II are stirred at RT for 2.5 h with 9 ml of trifluoroacetic acid in 9 ml of CH$_2$Cl$_2$. After concentration, the residue is taken up in ether twice and the solution is concentrated again. The residue is partitioned in ether/H$_2$O (pH 10), the aqueous phase is rendered acidic and extracted a further three times, and the combined organic phases are shaken twice with H$_2$O/NH$_4$Cl, twice with H$_2$O, once with H$_2$O/NaHCO$_3$ and once with H$_2$O/NH$_4$Cl, then dried over Na$_2$SO$_4$ and concentrated.

Yield:

2.2 g (86% of theory)
R=0.45 (CH$_2$Cl$_2$/MeOH=9:1)

PREPARATION EXAMPLES

Example 1 and Example 2 trans-2-{4-[(2-Cyclopropyl-benzimidazo-1H-yl-methyl]phenyl}-cyclohexane-1-carboxylic acid N-[(S)-phenylglycinol]amide

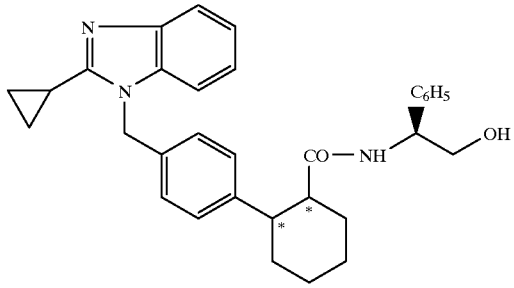

0.39 g (1 mmol) of trans-2-{4-[(2-cyclopropyl-benzimidazo-1H-yl)-methyl]phenyl}-cyclohexane-1-carboxylic acid is added to a solution of 0.14 g (1 mmol) of L-phenylglycinol in 10 ml of CH$_2$Cl$_2$, and the mixture is cooled to −10°C., treated with 0.23 g (1.2 mmol) of N'-(3-dimethylaminopropyl)-N-ethylcarbodiimide hydrochloride and 0.3 ml of triethylamine and stirred overnight at room temperature. For working up, it is treated with CH$_2$Cl$_2$, and shaken once each with a saturated aqueous solution of NH$_2$Cl, NaHCO$_3$ and (after additional shaking with H$_2$O) NaCl. After drying over Na$_2$SO$_4$, the mixture is concentrated and the product is chromatographed (silica gel 60, CH$_2$Cl$_2$/MeOH=20:1).

Yield:

0.16 g (0.32 mmol/R$_f$=0.60 (B) dia A (Example 1)
0.18 g (0.36 mmol/R$_f$=0.50 (B) dia B (Example 2)

The compounds shown in Table 1 are prepared in analogy to the procedure of Examples 1 and 2:

TABLE 1

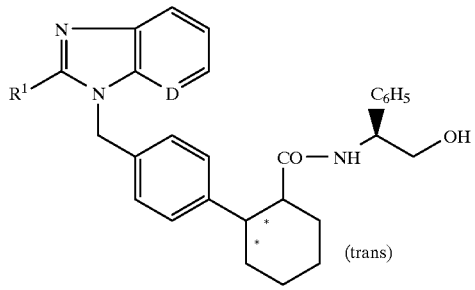

| Ex. No. | R$^1$ | D | Isomer | R$_f$(LM) |
|---|---|---|---|---|
| 3 | —CH(CH$_3$)$_2$ | N | dia A | 0.73 (B) |
| 4 | —CH(CH$_3$)$_2$ | N | dia B | 0.60 (B) |
| 5 | —CH(CH$_3$)$_2$ | CH | dia A | 0.53 (B) |
| 6 | —CH(CH$_3$)$_2$ | CH | dia B | 0.41 (B) |
| 7 | —C$_2$H$_5$ | N | dia A | 0.56 (B) |
| 8 | —C$_2$H$_5$ | N | dia B | 0.44 (B) |
| 9 | —C$_2$H$_5$ | CH | dia A | 0.70 (B) |
| 10 | —C$_2$H$_5$ | CH | dia B | 0.60 (B) |
| 11 | —C$_6$H$_5$ | CH | dia A | 0.77 (C) |
| 12 | —C$_6$H$_5$ | CH | dia B | 0.40 (C) |

Example 13 trans-2-[4-(2-Isopropylbenzimidazolyl-1H-methyl)phenyl]-cyclohexane-1-carbonyl(phenylglycine methyl ester)amide

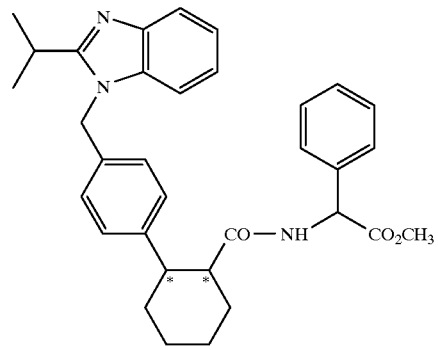

0.55 g (1.46 mmol) of the compound from Example III is dissolved at −30° C. under argon, treated with 0.81 ml (5.82 mmol) of triethylamine and 0.12 ml (1.6 mmol) of mesyl chloride in 12 ml of DME and stirred for 1 h. A solution of 0.35 g (1.7 mmol) of phenylglycine methyl ester, 0.18 g (1.46 mmol) of N,N-dimethylaminopyridine and 0.24 ml (1.72 mmol) of triethylamine, dissolved in 10 ml of DMF, is then added dropwise and the mixture is brought to RT with stirring overnight. It is then treated with H$_2$O and extracted three times with ethyl acetate. The combined organic phases are dried over Na$_2$SO$_4$ and concentrated, and the product is chromatographed on silica gel 60 (CH$_2$Cl$_2$/MeOH=20:1).

Yield:

0.37 g (48% of theory)
R$_f$=0.51 (CH$_2$Cl$_2$/MeOH=95:5)

Example 14 and Example 15 trans-2-[4-(2-Isopropylbenzimidazolyl-1H-methyl)phenyl]cyclohexane-1-carbonyl(phenylglycinamido)amide

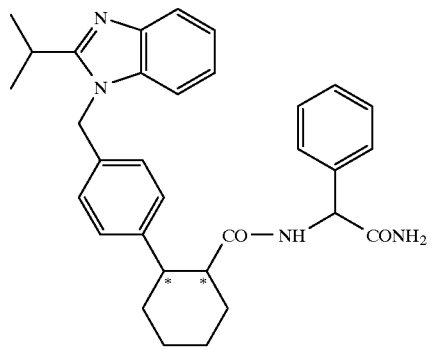

0.33 g (0.64 mmol) of the compound from Example 13 is dissolved in 1 ml of MeOH and stirred at RT for 5 days with 4 ml of $NH_3$-saturated MeOH. The precipitate is then separated off and the solution is concentrated. The residue is purified on silica gel 60 ($CH_2Cl_2$/MeOH/$NH_3$=100:5:0.3).

Yield:

61 mg (19% of theory) of dia A $R_f$=0.36 ($CH_2Cl_2$/MeOH= 9:1) Example 14

35 mg (11% of theory) of dia B $R_f$=0.32 ($CH_2Cl_2$/MeOH= 9:1) Example 15

The compounds shown in Table 2 are prepared in analogy to the procedure of Examples 14 and 15:

TABLE 2

| Ex. No. | $R^1$ | D | Isomer | Rf(LM) |
|---|---|---|---|---|
| 16 | cyclopropyl | CH | dia | 0.50 (A) |
| 17 | cyclopropyl | CH | dia B | 0.43 (B) |
| 18 | —$CH(CH_3)_2$ | N | dia A | 0.39 (B) |
| 19 | —$CH(CH_3)_2$ | N | dia B | 0.35 (B) |
| 20 | —$C_2H_5$ | N | dia | 0.51 (B) |
| 21 | —$C_2H_5$ | CH | dia A | 0.42 (B) |
| 22 | —$C_2H_5$ | CH | dia B | 0.38 (B) |
| 23 | —$C_6H_5$ | CH | dia | 0.85 (B) |

We claim:

1. A compound of the formula

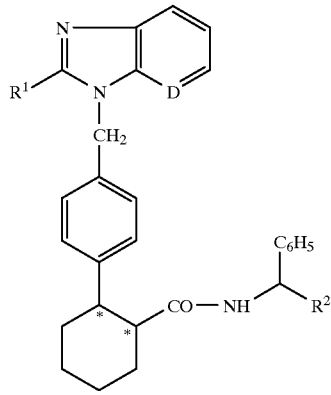

(I)

selected from the group consisting of compounds of the following table

| $R^1$ | D | $R^2$ | Isomer |
|---|---|---|---|
| —$CH(CH_3)_2$ | CH | —CO—$NH_2$ | dia A |
| —$CH(CH_3)_2$ | CH | —CO—$NH_2$ | dia B |
| cyclopropyl | CH | —CO—$NH_2$ | dia |
| cyclopropyl | CH | —CO—$NH_2$ | dia B |
| —$C_2H_5$ | CH | —CO—$NH_2$ | dia A |
| —$C_2H_5$ | CH | —CO—$NH_2$ | dia B |
| —$C_6H_5$ | CH | —CO—$NH_2$ | dia | or a salt thereof.

2. The compound according to claim 1, wherein $R^1$ is $C_6H_5$

D is CH; and $R^2$ is CO—$NH_2$.

3. The compound according to claim 1, which has the formula

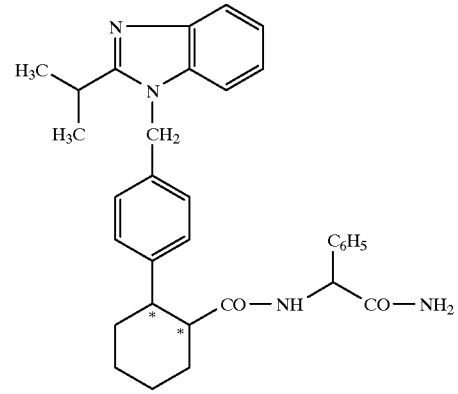

or a salt thereof.

4. The compound according to claim 1, which has the formula

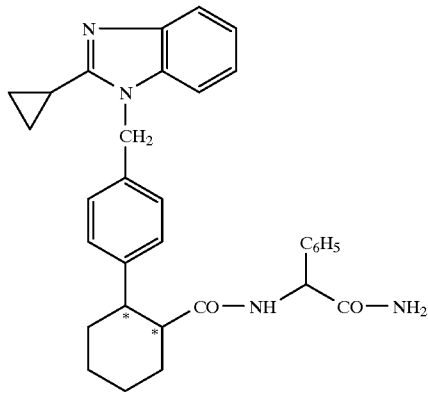

or a salt thereof.

5. The compound according to claim 1, which has the formula

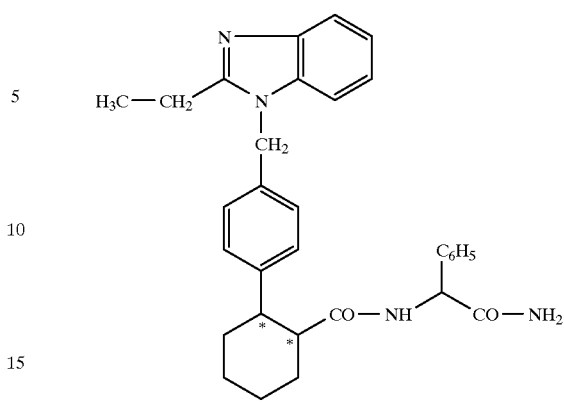

or a salt thereof.

6. A composition for inhibiting cell proliferation of the smooth muscle cells which comprises an effective amount therefor of a compound according to claim 1 and a diluent.

7. A method of treating retenosis cells in a patient in need thereof which comprises administering an effective amount therefor of a compound according to claim 1 to said patient.

8. A method of treating arteriosclerosis in a patient in need thereof which comprises administering an effective amount therefor of a compound according to claim 1 to said patent.

9. A method of inhibiting cell proliferation of the non-cancerous smooth muscle cells in a patient in need thereof which comprises administering an effective amount therefor of a compound according to claim 1 to said patient.

* * * * *